United States Patent
Kim et al.

(10) Patent No.: US 7,022,347 B2
(45) Date of Patent: Apr. 4, 2006

(54) RESTORATIVE AND GRAFTING MATERIAL FOR HARD TISSUE DEFECTS PREPARED FROM ANIMAL TEETH

(76) Inventors: Su-Gwan Kim, Oral and Maxillofacial Surgery Department, Chosun University Dental Hospital, 2nd Floor, 421 Seoseok-dong, Dong-ku, Gwangju (KR); Young Guyn Kim, #1-103 Hanseong Villa, 46 Bundang-dong, Bundang-ku, Seongnam-si, Kyunggi-do (KR)

( * ) Notice: Subject to any disclaimer, the term of this patent is extended or adjusted under 35 U.S.C. 154(b) by 0 days.

(21) Appl. No.: 10/717,801

(22) Filed: Nov. 19, 2003

(65) Prior Publication Data

US 2004/0202984 A1    Oct. 14, 2004

(30) Foreign Application Priority Data

Apr. 8, 2003    (KR) .................... 10-2003-0021838

(51) Int. Cl.
*A61C 5/00*    (2006.01)
*A61K 9/00*    (2006.01)
*A61K 9/14*    (2006.01)
*A61K 9/50*    (2006.01)
*A61K 35/32*    (2006.01)

(52) U.S. Cl. .................... 424/549; 424/400; 424/489; 424/501; 433/215

(58) Field of Classification Search ............ 424/93.72; 435/325, 400
See application file for complete search history.

(56) References Cited

U.S. PATENT DOCUMENTS

| | | | | | |
|---|---|---|---|---|---|
| 2,508,816 | A | * | 5/1950 | De Ment | 524/10 |
| 3,075,880 | A | * | 1/1963 | Roth | 424/602 |
| 5,217,375 | A | * | 6/1993 | Oden et al. | 433/218 |
| 5,733,545 | A | * | 3/1998 | Hood, III | 424/93.72 |

* cited by examiner

*Primary Examiner*—David M. Naff
*Assistant Examiner*—Deborah K. Ware
(74) *Attorney, Agent, or Firm*—Bachman & LaPointe, P.C.

(57) ABSTRACT

The restorative and grafting material for reconstruction of hard tissue defects and the fabrication method of the same are provided. In particular, the restorative and grafting material of this invention is produced by the steps of cleansing, decoloration (bleaching), burning, and pulverization of collected animal teeth.

4 Claims, 3 Drawing Sheets

RESTORATIVE AND GRAFTING MATERIAL FOR HARD TISSUE DEFECTS PREPARED FROM ANIMAL TEETH

TECHNICAL FIELD

The present invention relates to a restorative and grafting material for hard tissue defect in human, more precisely, to a restorative and grafting material prepared by the steps of collecting animal teeth that are obtained during slaughtering, cleaning, incinerating at high temperature, pulverizing to powder and removing impurities and organic substances by centrifugation and chemical treatment and a fabrication method of the same.

BACKGROUND OF ART

In order to restore hard tissue defects of the jaw of oral cavity, grafting materials fabricated by autogenous bone, homogenous bone, heterogenous bone or bone-substitute materials such as hydroxyapatite, tricalcium phosphate and bioglass have been developed and clinically used in general, and further experiments and studies have also been going on.

The restorative mechanism by grafting bone or substitute materials for bone includes the stages of osteogenesis, bone induction and bone conduction, so autogenous bone having all the three phenomena has been believed to be the best grafting material for the treatment of hard tissue defects. However, autogenous bone is not the best grafting material in a real clinical use. The operations such as bone intensification, restoration for cranial bone defects, etc. require materials that are not absorbed rightly after grafting and stay longer as they are. Thus, other substitute materials for bone or autogenous bone treated with immune response inhibitor have been selectively used for such operations.

The disadvantages of using autogenous bone as a grafting material for restoration of hard tissue defect was that it carried secondary defects in donor site and was absorbed after grafting as predicted. In order to avoid those problems, the use of homogenous bone or heterogenous bone was studied and applied clinically. But it still caused problems after grating such as retardation of bone reorganization, infection of viral diseases and immunological rejection.

On the other hand, hydroxyapatite, tricalcium phosphate and bioglass, which were developed as substitute materials for bone, had limitations in clinical use because of difficulties in processing, high price and having bone conduction ability only. And their mobility after grafting made matter worse.

Every grafting material should be in a right position stably unmoved for bone treatment. Thus, mobility should be reduced, for which close suture, tissue adhesives and a special apparatus have been used. However, close suture take a pretty long operation time and is not suitable for wound, and using tissue adhesives costs much.

The method using a special apparatus also has problems that huge time and expense were required for making the apparatus.

The solution for the above problems is presented in Korea patent #261034 "Teeth gypsum and the preparation method of the same" which was applied by the present inventors and registered on Apr. 15, 2000.

The said teeth gypsum is prepared by the steps of cleaning the teeth collected from dental clinics, incinerating, pulverizing to teeth powder after removing impurities and mixing the powder with medical gypsum at the required ratio.

The materials for making the teeth gypsum should be collected from dental clinics or hospitals, so that the amount of the materials are too short to be widely used for the treatment.

BRIEF DESCRIPTION OF THE DRAWINGS

The application of the preferred embodiments of the present invention is best understood with reference to the accompanying drawings, in which like reference numerals are used for like and corresponding parts, wherein.

DISCLOSURE OF INVENTION

Figure 1:
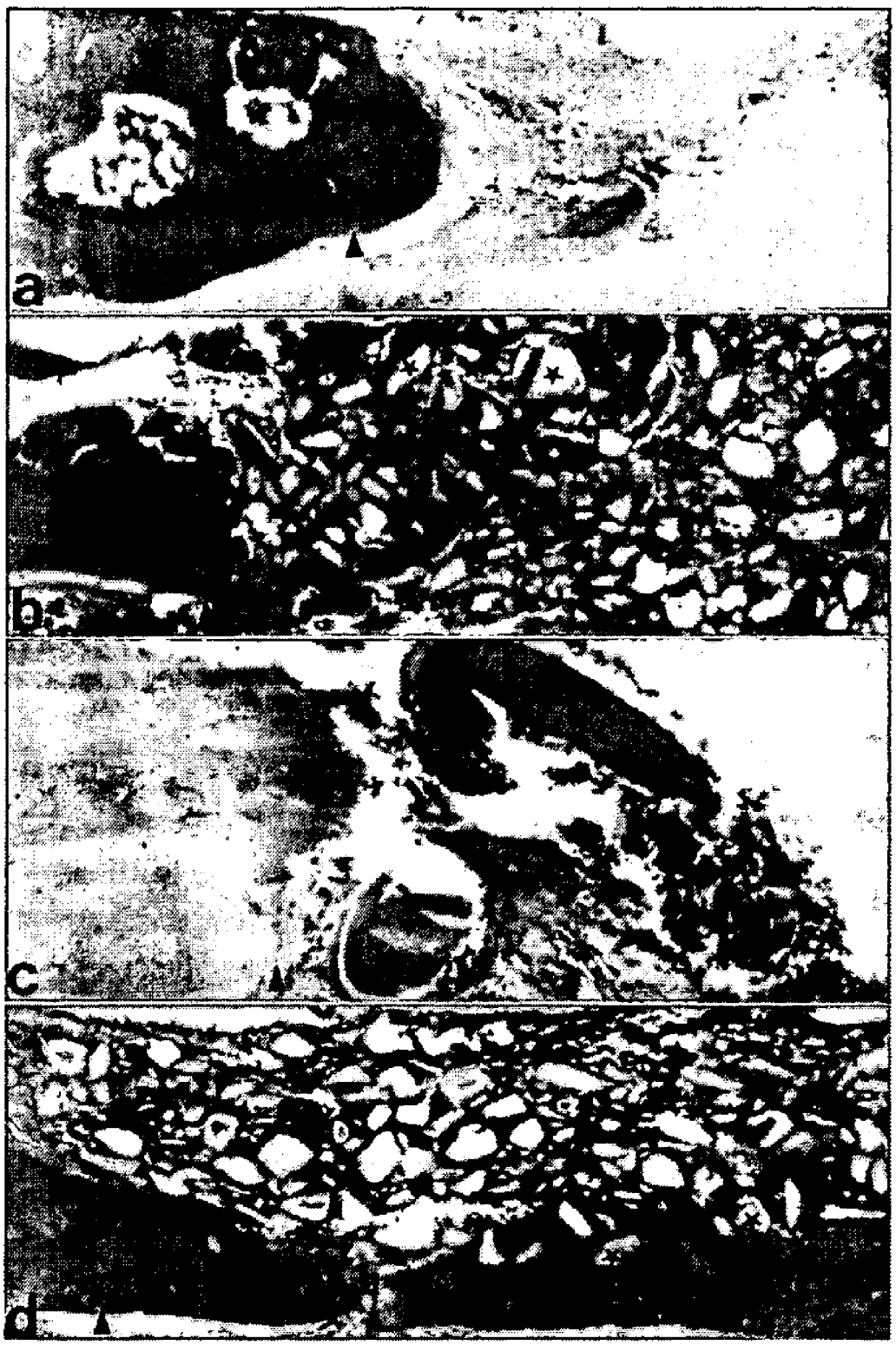
FIG. 1 is a picture of optical microscope that observes a new bone formation in 4 weeks after a grafting material of the present invention is grafted on bone defect area(×125).

It is an object of the present invention to mass-supply restorative and grafting materials for hard tissue defects by preparing the restorative and grafting materials using animal teeth, especially mammal teeth collected during slaughtering, instead of human teeth.

It is another object of the present invention to provide harmless restorative and grafting materials for hard tissue defects properly sterilized.

To achieve the above objects, the present invention provides a fabrication method for restorative and grafting materials for hard tissue defects using animal teeth, which comprises the steps of 1) collecting animal teeth, waste matters of slaughter house; 2) removing soft tissues by washing the teeth with ultrasonicator after dipping the collected teeth in hydrogen peroxide for a while and drying thereof, sterilizing thereof with ethyl alcohol and bleaching thereof; 3) incinerating thereof at high temperature; 4) pulverizing the incinerated teeth; 5) removing impurities by treating the pulverized teeth powder at high temperature again; and 6) sterilizing the teeth powder with ethylene gas.

The present invention also provides restorative and grafting materials for hard tissue defects using animal teeth, which are characterized by being prepared by the above method of the invention.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Scores of thousands of livestock such as cattle and pigs are slaughtered every year and their teeth are nothing but waste.

Thus, it is easy to collect such animal teeth without expense.

The collected animal teeth from butchery ought to be washed to remove soft tissues and impurities.

Precisely, the method for washing and removing soft tissues includes the steps of dipping the collected animal teeth in hydrogen peroxide for 2–3 days, sterilizing with alcohol and bleaching. Further, the sterilized animal teeth are washed with an ultrasonicator in 20–60 Hz for 1 hour to remove soft tissues and impurities completely.

In order to avoid the possible immunological rejection occurring after transplanting the prepared animal teeth into human, the animal teeth should be incinerated at 1000–1500° C. for at least 90–180 minutes. Human immune system is different from that of animals. Thus, when animal teeth are transplanted into human, rejection by immune system follows. In order to suppress the immunological rejection, organic matters in animal teeth should be incinerated at high temperature for a long time.

The incinerated teeth are pulverized into powder, which are made to be even size powder using a mesh gauge. It is important to make the powder even and generally the powder is prepared by 70–120 μm in size, for which 70 μm mesh gauge, 90 μm mesh gauge, and 120 μm mesh gauge are used to filter the powder.

The prepared even size animal teeth powder has black or dark gray color, thus, when it is used for the restoration of hard tissue defects as it is, soft tissues of restored region change black. Especially when it is used for teeth, it had better be decolorized into white for better aesthetic result. In addition, the teeth powder might have impurities resulted from incomplete incineration, which can cause inflammation after transplantation. Therefore, the present inventors treat the teeth powder at over 1200° C. at least for 1 hour to remove the impurities and to bleach completely.

In order to eliminate any harmful substance, the present inventors sterilize the teeth powder again even after removing impurities and bleaching completely.

At this time, ethylene oxide (EO) gas is used for sterilization. Precisely, the teeth powder is sterilized thoroughly by treating it with ethylene oxide gas for 11–13 hours, keeping the concentration of the gas 1.0–3.0 kg/cm$^2$, resulting in the preparation of a restorative and grafting material for hard tissue defects.

The restorative and grafting material for hard tissue defects prepared by using animal teeth is limited in use. That is, the teeth powder itself cannot stay stably in right position owing to its mobility, causing a problem in vivo grafting.

Therefore, it is recommended to mix it with medical gypsum, concentrated platelets, dental porcelain or acrylic resin at the required ratio for better use in grafting for needed part of human body.

For example, the teeth powder is mixed with medical gypsum at the ratio of 1:1 or 2:1, leading to the preparation of a grafting material having minimum mobility.

In order to make a grafting material by mixing the teeth powder with concentrated platelets, 5–15 cc of the concentrated platelets are mixed with the teeth powder, leading to the preparation of a grafting material having maximum bone formation and healing activity. The grafting material containing concentrated platelets can be widely used in restoration of jaw defect, restoration of implant area defect, restoration of enucleated cystic cavity, prevention of alveolar bone absorption after tooth extraction, alveolar ridge augmentation for dental prosthesis, treatment of periodontal diseases, GBR, GTR, etc.

In case of mixing dental porcelain or acrylic resin, the preferred mixing ratio of teeth powder to porcelain is 1:1–4:1 or 1:1–1:4. It is possible to prepare the grafting material having the same color as that of teeth of patients by regulating the mixing ratio. The use of the dental porcelain or acrylic resin mixed grafting material is also in variety, for example, for the treatment of dental caries, teeth crown fracture, teeth abrasion, erosion, etc.

As an example of the use of restorative and grafting material for hard tissue defects prepared by using animal teeth, the experiment with white mice is explained precisely hereinafter.

The present inventors used 12-week-old female white mice for the experiment. The mice were divided into two groups: one consisted of those having ovariectomy (experimental group) and the other consisted of those not having ovariectomy (control group), which were subdivided into two groups again: the group treated with the restorative and grafting material of the present invention and the group not treated with the material after formation of bone defects. Each group contained 15 mice.

The present inventors used a grafting material prepared by mixing the restorative and grafting material of the invention with dental soft gypsum at the weight ratio of 2:1 using physiological saline.

Firstly, the white mice were anesthetized and their ovaries were extracted. Seven weeks later, the present inventors cut the middle of cranial bone and took off the cranial bone 9 mm in diameter. Then, grafted the grafting material, sutured the periosteum. So did tissue. Sacrificed the mice on the 4$^{th}$, 8$^{th}$ and 16$^{th}$ week as seen in Table 1 and observed the conditions of the grafting material.

As for the group that was not treated with grafting material, the present inventors removed a part of cranial bone to induce bone defects just like the experimental group, and then sutured without grafting. Sacrificed the mice also on the 4$^{th}$, 8$^{th}$ and 16$^{th}$ week as seen in Table 1 and observed the conditions of cranial bone eliminated area.

TABLE 1

| | | Experimental data | | | | |
|---|---|---|---|---|---|---|
| | Index | | 4$^{th}$ week | 8$^{th}$ week | 16$^{th}$ week | Total |
| Ovary removed | Not grafted | Group 1 | 5 | 5 | 5 | 15 |
| | Grafted with grafting material | Group 2 | 5 | 5 | 5 | 15 |
| Ovary not removed | Not grafted | Group 3 | 5 | 5 | 5 | 15 |
| | Grafted with grafting material | Group 4 | 5 | 5 | 5 | 15 |
| | Total | | 20 | 20 | 20 | 60 |

Sacrificed the white mice of the experimental group as scheduled, and then took samples including bone of grafting area. Fixed the samples in 10% neutral formalin for 72 hours, after which decalcificated with nitric acid for 4 hours. Cut the samples 3 mm thick and washed with running water. Treated the tissues of the samples using an autoprocessing machine(Hypercentre XP). Embedded the treated tissues in paraffin, after which cut them by 4–5 μm thick. Stained them with hematoxylin-eosin and Goldner's trichrome, and then observed with an optical microscope.

Statistical analysis was performed by nonparametric Wilcoxon rank test using SPSS. The present inventors regarded as statistically significant when the p value was under 0.05.

Figure 3:
FIG. 3 is a picture of optical microscope that observes a new bone formation in 16 weeks after a grafting material of the present invention is grafted on bone defect area(×250).

As a result of the observation, the subgroup of group 1 sacrificed on the 4$^{th}$ week showed partial bone formation around limbic part of bone defect area. Another subgroup of group 1 sacrificed on the $8^{th}$ week showed better bone formation than the above group, which was not a statistically significant result, though. Better bone formation was seen in the 16-week group compared with the 8-week group (see FIG. 3a) with a statistical significance compared with the 4-week group (p=0.0149).

The subgroup of group 2 sacrificed on the $4^{th}$ week showed bone formation around limbic part of bone defect area and near grafting material, which was statistically significant promotion of bone formation (p=0.0337, comparing to the control group)(see FIG. 1b). Another subgroup of group 2 sacrificed on the $8^{th}$ week showed better bone formation, which was not a statistically significant. Besides, lamellar bone formation and the fusion of bony islands that were newly formed around grafting material were also observed in that group(see FIG. 2b). The subgroup of group 2 sacrificed on the $16^{th}$ week showed matured bone formation, the fusion of bony islands and the increase of lamellar bone, which were, though, not a statistically significant. But the remarkable increase of new bone formation was also observed in that group, comparing to the group sacrificed on the $4^{th}$ group, which was statistically significant (p=0.000386)(see FIG. 3b).

The subgroup of group 3 that was sacrificed on the $4^{th}$ week showed partial bone formation in limbic part of bone defect area(see FIG. 1c).

Figure 2:
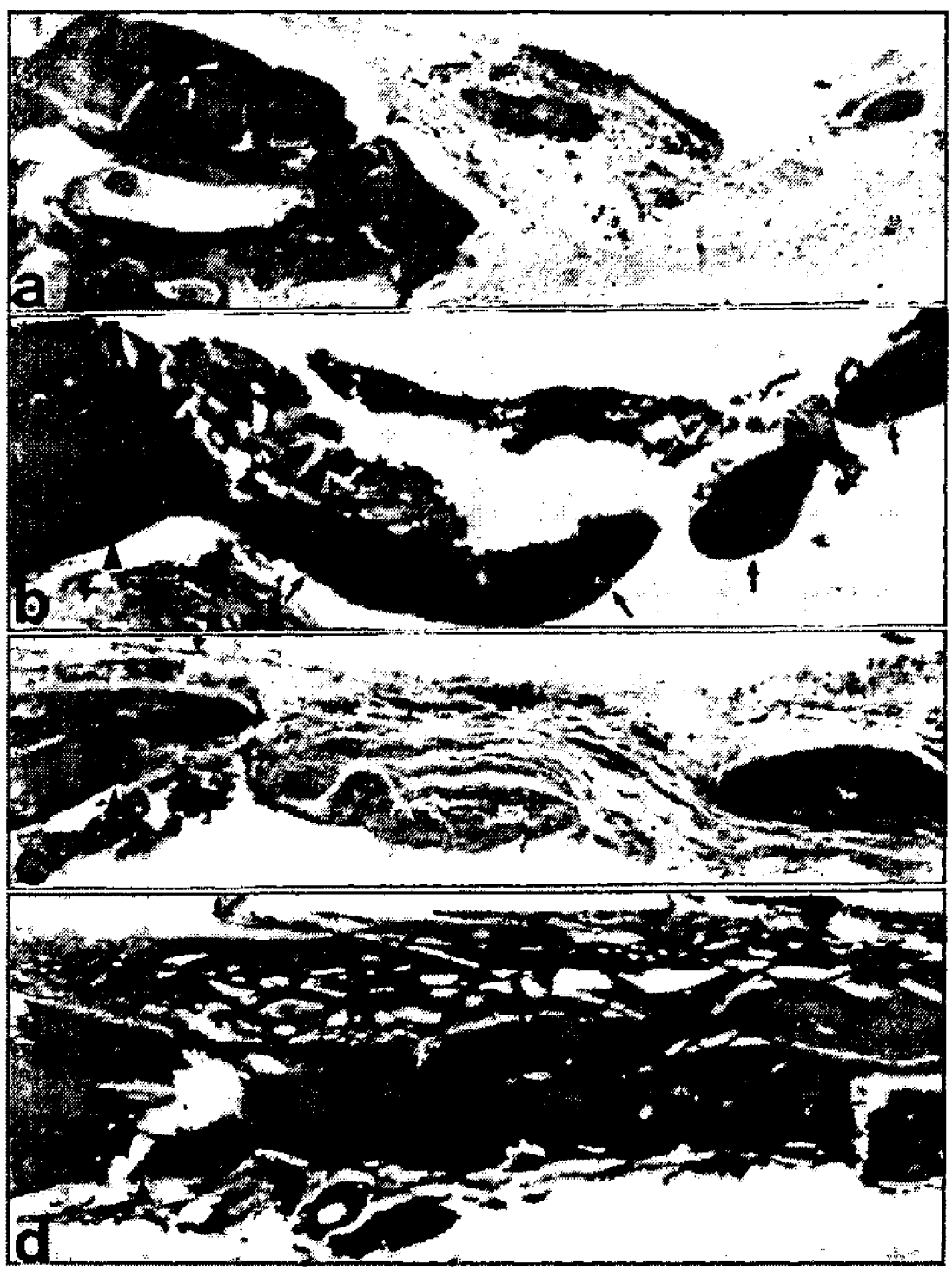
FIG. 2 is a picture of optical microscope that observes a new bone formation in 8 weeks after a grafting material of the present invention is grafted on bone defect area(×250).

The subgroup of group 3 sacrificed on the $8^{th}$ week showed better bone formation than the subgroup sacrificed on the $4^{th}$ week, which was not a statistically significant, either (see FIG. 2c).

The subgroup of group 3 sacrificed on the $16^{th}$ week showed rather meaningful bone formation (p=0.00295). Compared with the subgroup sacrificed on the $8^{th}$ week, the subgroup sacrificed on the $16^{th}$ week showed more matured bone formation, the increased lamella bone formation and the fusion of bony islands. (see FIG. 3c).

The subgroup of group 4 sacrificed on the $4^{th}$ week showed bone formation around limbic part of bone defect area and grafting material, which was more than the group 3 (p=0.0337). Compared with a control group, new bone formation was increased, which was not a statistically significant, though(see FIG. 1d). The subgroup of group 4 sacrificed on the $8^{th}$ week showed much better bone formation than the subgroup sacrificed on the $4^{th}$ week, which was not important statistically, either. Partial lamellar bone formation and the fusion between bony islands, which were newly formed around grafting material, were additionally observed in that group. Compared with group 3, bone formation was increased without statistical significance and so was when compared with group 1 and group 2(see FIG. 2d). The subgroup of group 4 sacrificed on the $16^{th}$ week showed statistically significant bone formation, compared with the subgroups sacrificed on the $4^{th}$ week and $8^{th}$ week (p=0.01822 and p=0.00026, respectively). Newly formed bone was more mature in that group and the fusion between bony islands and the increase of lamellar bone formation were additionally observed therein. The increase of new bone formation was statistically significant, compared with group 1 and group 2 (p=0.04882)(see FIG. 3d).

It was reported as an example of inducing osteoporosis after menopause that the ovary of an about 12 week old white mouse was extracted and the animal was confirmed to have osteoporosis after 7 weeks. Cranial bone defects were made in the above experimental group already induced with osteoporosis and then the grafting material was treated thereto. Then, investigated the efficacy of the restorative and grafting material for hard tissue defects of the present invention.

As stated above, as for group 2, induced bone defects after inducing osteoporosis by extracting ovary and then treated with the grafting material and as for group 4, induced bone defects without extracting ovary and treated with the grafting material. Resultingly, the grafting material prepared by mixing the restorative and grafting material for hard tissue defects with dental gypsum was confirmed to reduce immunological rejection and inflammation, to have bone conduction activity and good absorptivity, and to be manipulated with easy.

As explained hereinbefore, the restorative and grafting material for hard tissue defects of the present invention takes advantage of animal teeth, so that the raw materials can be easily and fully supplied and the production costs less.

Besides, the restorative and grafting material of the present invention is harmless for human since it is prepared by the steps of bleaching, sterilization, incineration, pulverization and re-sterilization. The material also provides great advantages such as bone conduction capacity like autogenous bone, no inflammation or no immunological rejection response that occurs frequently after grafting.

Moreover, the restorative and grafting material for hard tissue defects of the present invention can be mix-used with other biomaterials and grafting materials in various types and intensity, resulting in the convenience in use regardless of the areas of hard tissue defects.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A restorative and grafting material for hard tissue defects using animal teeth, which is prepared by a method comprising the steps of:
    collecting animal teeth;
    removing soft tissues from the animal teeth;
    sterilizing the animal teeth;
    incinerating the sterilized animal teeth at high temperature;
    pulverizing the incinerated teeth to teeth powder;
    removing impurities and bleaching the teeth powder by treating the teeth powder at high temperature;
    re-sterilizing the teeth powder to provide for the restorative and grafting material in powder form; and
    mixing the re-sterilized teeth powder with a material selected from the group consisting of medical gypsum, concentrated platelets, dental porcelain, acrylic resin and mixtures thereof to attach defect area.

2. The restorative and grafting material for hard tissue defects using animal teeth according to claim 1, wherein the re-sterilized teeth pewder is mixed with medical gypsum at the ratio of 1:1–2:1.

3. The restorative and grafting material for hard tissue defects using animal teeth according to claim 1, wherein the re-sterilized teeth powder is mixed with 5–15 cc of concentrated platelets.

4. The restorative and grafting material for hard tissue defects using animal teeth according to claim 1, wherein the re-sterilized teeth powder is mixed with dental porcelain or acrylic resin at the ratio of 1:1–1:4 or 1:1–4:1.

* * * * *